United States Patent
Eom et al.

(10) Patent No.: US 9,814,548 B2
(45) Date of Patent: Nov. 14, 2017

(54) THREE-DIMENSIONAL ORAL CAVITY SCAN DEVICE USING PIEZOELECTRIC ELEMENT BASED PATTERN MODULE AND VARIABLE FOCUS LENS

(71) Applicant: KOREA PHOTONICS TECHNOLOGY INSTITUTE, Gwangju (KR)

(72) Inventors: Joo Beom Eom, Gwangju (KR); Jaesung Ahn, Gwangju (KR); Byeong Il Lee, Gwangju (KR); In Hee Shin, Gwangju (KR); Anjin Park, Gwangju (KR); Byeong Ha Lee, Gwangju (KR)

(73) Assignee: KOREA PHOTONICS TECHNOLOGY INSTITUTE, Gwangju (KR)

( * ) Notice: Subject to any disclaimer, the term of this patent is extended or adjusted under 35 U.S.C. 154(b) by 0 days.

(21) Appl. No.: 15/322,940

(22) PCT Filed: Apr. 5, 2016

(86) PCT No.: PCT/KR2016/003511
§ 371 (c)(1),
(2) Date: Dec. 29, 2016

(87) PCT Pub. No.: WO2016/171412
PCT Pub. Date: Oct. 27, 2016

(65) Prior Publication Data
US 2017/0156826 A1    Jun. 8, 2017

(30) Foreign Application Priority Data

Apr. 22, 2015   (KR) .................. 10-2015-0056711

(51) Int. Cl.
*A61C 9/00*    (2006.01)
*G01B 11/25*    (2006.01)
(Continued)

(52) U.S. Cl.
CPC ............ *A61C 9/006* (2013.01); *A61B 1/0019* (2013.01); *A61B 1/247* (2013.01); *A61B 5/0062* (2013.01);
(Continued)

(58) Field of Classification Search
CPC ..... A61C 9/0053; A61C 9/006; A61C 9/0066; A61C 9/0073; A61C 9/008; A61C 9/04;
(Continued)

(56) References Cited

U.S. PATENT DOCUMENTS 4,575,805 A * 3/1986 Moermann ........ A61C 13/0004
                                              250/237 G
6,885,464 B1 * 4/2005 Pfeiffer ................ A61B 5/0064
                                              356/602
(Continued)

FOREIGN PATENT DOCUMENTS

JP    2010-148860 A    7/2010
KR    10-2010-0087629 A    8/2010
(Continued)

*Primary Examiner* — Gordon J Stock, Jr.
(74) *Attorney, Agent, or Firm* — Rabin & Berdo, P.C.

(57) ABSTRACT

The present invention relates to a three-dimensional oral cavity scan device for a digital impression that obtains a three-dimensional image by processing a two-dimensional image acquired by photographing a three-dimensional subject in an oral cavity. The device includes: a pattern mask converting parallel light incident thereto into structured light; a piezoelectric plate where a mechanical vibration is generated on a surface thereof by an AC voltage applied thereto; and a power supply unit applying the AC voltage to the piezoelectric plate, wherein the piezoelectric plate moves the pattern mask in a longitudinal direction of the piezoelectric plate by using the mechanical vibration. The device can reduce noise and vibration by moving the pattern mask with an electrical method. In addition, the device can
(Continued)

accurately measure depth of teeth by electrically controlling a focal length of structured light projected on the teeth.

10 Claims, 4 Drawing Sheets

(51) Int. Cl.
 *A61B 5/00* (2006.01)
 *A61B 1/00* (2006.01)
 *A61B 1/247* (2006.01)
(52) U.S. Cl.
 CPC ............ *A61B 5/0088* (2013.01); *A61C 9/008* (2013.01); *A61C 9/0066* (2013.01); *G01B 11/25* (2013.01); *G01B 11/2518* (2013.01)
(58) Field of Classification Search
 CPC ....... G01B 11/002; G01B 11/22; G01B 11/24; G01B 11/2441; G01B 11/25; G01B 11/2513; G01B 11/2518; G01B 11/2522; G01B 11/2527; G01B 11/2531; G01B 11/2536; G01B 11/254; A61B 1/00163; A61B 1/00172; A61B 1/00188; A61B 1/0019; A61B 1/04; A61B 1/05; A61B 1/0646; A61B 1/0669; A61B 1/24; A61B 1/247; A61B 5/0088; A61B 5/1077; A61B 5/0062; A61B 5/0064; A61B 5/0066; A61B 5/0068; A61B 5/4547
 See application file for complete search history.

(56) References Cited

U.S. PATENT DOCUMENTS

| | | | |
|---|---|---|---|
| 8,279,450 B2 * | 10/2012 | Oota | .................. A61B 1/0019 356/601 |
| 2005/0243330 A1 | 11/2005 | Magarill et al. | |
| 2010/0157019 A1 * | 6/2010 | Schwotzer | .............. A61B 1/24 348/46 |
| 2010/0189341 A1 | 7/2010 | Oota et al. | |
| 2010/0311005 A1 | 12/2010 | Liang | |
| 2015/0029309 A1 * | 1/2015 | Michaeli | ............ G02B 21/0028 348/46 |

FOREIGN PATENT DOCUMENTS

| | | |
|---|---|---|
| KR | 10-2010-0130559 A | 12/2010 |
| KR | 10-2012-0050854 A | 5/2012 |
| KR | 10-2013-0019296 A | 2/2013 |

* cited by examiner

THREE-DIMENSIONAL ORAL CAVITY SCAN DEVICE USING PIEZOELECTRIC ELEMENT BASED PATTERN MODULE AND VARIABLE FOCUS LENS

TECHNICAL FIELD

The present invention relates to an oral cavity scan device for accurately obtaining an image of teeth. More particularly, the present invention relates to an oral cavity scan device obtaining a three-dimensional shape of teeth by using structured light.

BACKGROUND ART

Generally, a three-dimensional oral cavity scan device photographs a three-dimensional subject in an oral cavity by using a digital impression. The three-dimensional oral cavity scan device obtains a three-dimensional image by processing a two-dimensional image that is obtained by photographing a subject. Development of the three-dimensional oral cavity scan device has been in conjunction with it being connected to a milling machine and a 3D printer.

The three-dimensional oral cavity scan device measures teeth and gums positioned in an oral cavity by using a three-dimensional camera, and obtains a three-dimensional shape of teeth by using a CAD/CAM system. The three-dimensional oral cavity scan device is a device obtaining a three-dimensional image that is identical to a real image of the subject by using a computer, and showing shapes of teeth and oral tissue in case of a dental treatment such as dental recovery, prosthetic dentistry, etc.

The three-dimensional oral cavity scan device enables an optical source to emit light to a subject, and obtains a two-dimensional image by using light reflected from the subject, and obtains a three-dimensional image by combining obtained two-dimensional images. The three-dimensional oral cavity scan device uses an analysis method such as conventional confocal microscopy, a triangulation method, an optical coherence tomography method, accordion fringe interferometry, an active wavefront sampling method, etc. The development of the analysis method has been in conjunction with it being connected to a milling machine and a 3D printer.

In this regard, as a document of related art, an oral cavity scanner measuring teeth by using a triangulation method is disclosed in Korean Patent Application Publication No. 10-2012-0050854. FIG. 1 is a view showing a conventional oral cavity scanner. Referring to FIG. 1, the conventional oral cavity scanner 100' (paragraph [0076] of the document of related art) includes an insert body 210, a body 220, a guide 230, an optical system 240, an optical system driving member 250, an optical system suspending member 260, an optical output element 270, an optical sensing element 280, a control module 290, a data processing module 300, etc.

The above-described conventional technology uses a mechanical optical output method moving the optical output element 270 in a slidable manner by using the optical system driving member 250 or the optical system suspending member 260. However, the above-described conventional technology has problems such as a large size of the conventional oral cavity scanner, noise, and vibrations.

DOCUMENTS OF RELATED ART

Patent Document (Patent Document 1) Korean Patent Application Publication No. 10-2012-0050854

DISCLOSURE

Technical Problem

The present invention has been proposed to solve the problems in the related art, and is intended to operate an optical output element by using an electrical method so as to remove vibrations, noise, etc. that are generated in the case of a mechanical optical output method. In addition, the present invention is intended to propose a device adjusting a focal distance of structured light projected on teeth by using an electrical method so as to accurately measure depth of the teeth.

Technical Solution

In order to achieve the above object, the present invention provides an oral cavity scan device obtaining a three-dimensional shape of teeth by using structured light, the device including: a pattern mask converting parallel light incident thereto into the structured light; a piezoelectric plate where a mechanical vibration is generated on a surface thereof by an AC voltage applied thereto; and a power supply unit applying the AC voltage to the piezoelectric plate, wherein the piezoelectric plate moves the pattern mask in a longitudinal direction of the piezoelectric plate by using the mechanical vibration generated on the surface of the piezoelectric plate.

Desirably, the pattern mask may include: a light transmission line through which the parallel light passes; and a light shielding line blocking the parallel light, wherein the light transmission line and the light shielding line may be alternately arranged in the pattern mask.

Desirably, the oral cavity scan device may further include an offset lens to which the structured light is incident, with a concave curvature formed in the offset lens; and a reflection mirror reflecting the structured light in a direction toward a subject, wherein the offset lens may reduce a focal distance of the structured light.

Desirably, the oral cavity scan device may further include a variable focus lens adjusting the reduced focal distance of the structured light penetrating the offset lens.

Desirably, the variable focus lens may include: a first liquid layer that is conductive; a second liquid layer that is insulative; and a plurality of electrodes to which voltage or current is applied.

Desirably, the variable focus lens may be configured such that, when the voltage or the current is applied to the plurality of electrodes, the first liquid layer and the second liquid layers that are arranged in parallel to each other are adjusted, so the variable focus lens may control the reduced focal distance Desirably, the variable focus lens may enable reflected light reflected from the subject to be incident to the offset lens so as to obtain an image of the teeth.

Desirably, the piezoelectric plate may be a PZT (plumbum zirconate titanate) ceramic element.

Advantageous Effects

According to the present invention, the piezoelectric plate generates mechanical vibrations by applying an electric field and moves the pattern mask, thereby reducing noise and vibrations.

In addition, according to the present invention, the variable focus lens electrically controls the focal distance of the structured light projected on teeth, thereby accurately measuring depth of the teeth. In this case, the structured light is controlled by using the piezoelectric plate and the variable focus lens, and oral cavity scan device can be provided in a small size.

BEST MODE

Figure 1:
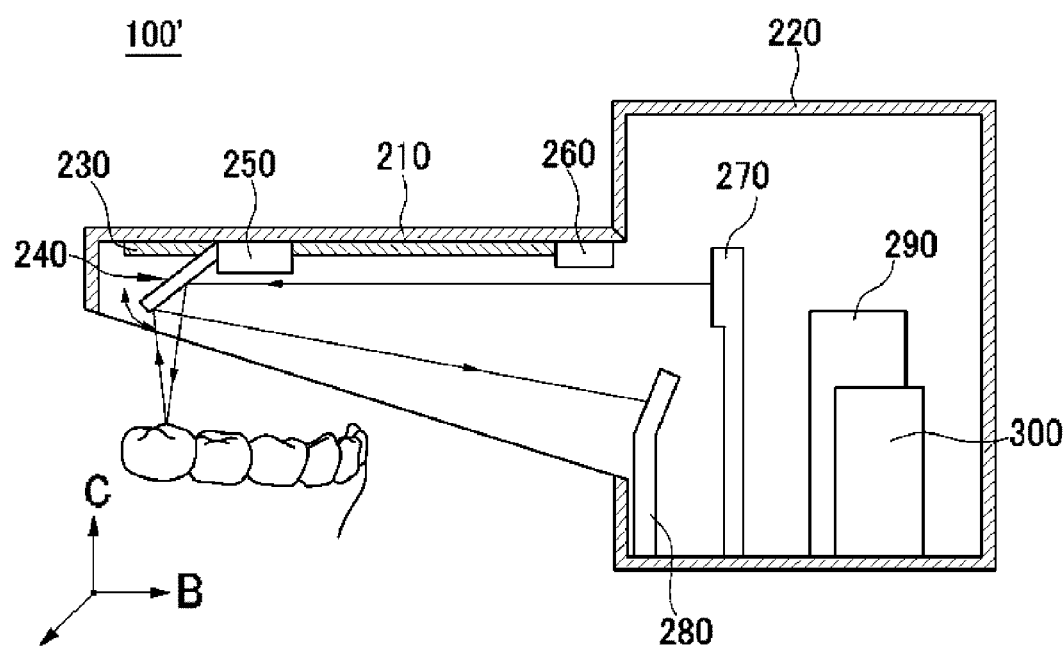
FIG. 1 is a view showing a conventional oral cavity scanner.

Hereinafter, exemplary embodiments of the present invention will be described in detail with reference to the accompanying drawings. However, the present invention is not limited or restricted by the embodiments. Throughout the drawings, the same reference numerals will refer to the same or like parts.

Objects and effects of the present invention will be naturally understood or become apparent from the following description, and the objects and effects of the present invention are not restricted by the following description. Further, in the following description of the present invention, a detailed description of known functions and configurations incorporated herein will be omitted when it may make the subject matter of the present invention rather unclear.

Figure 2:
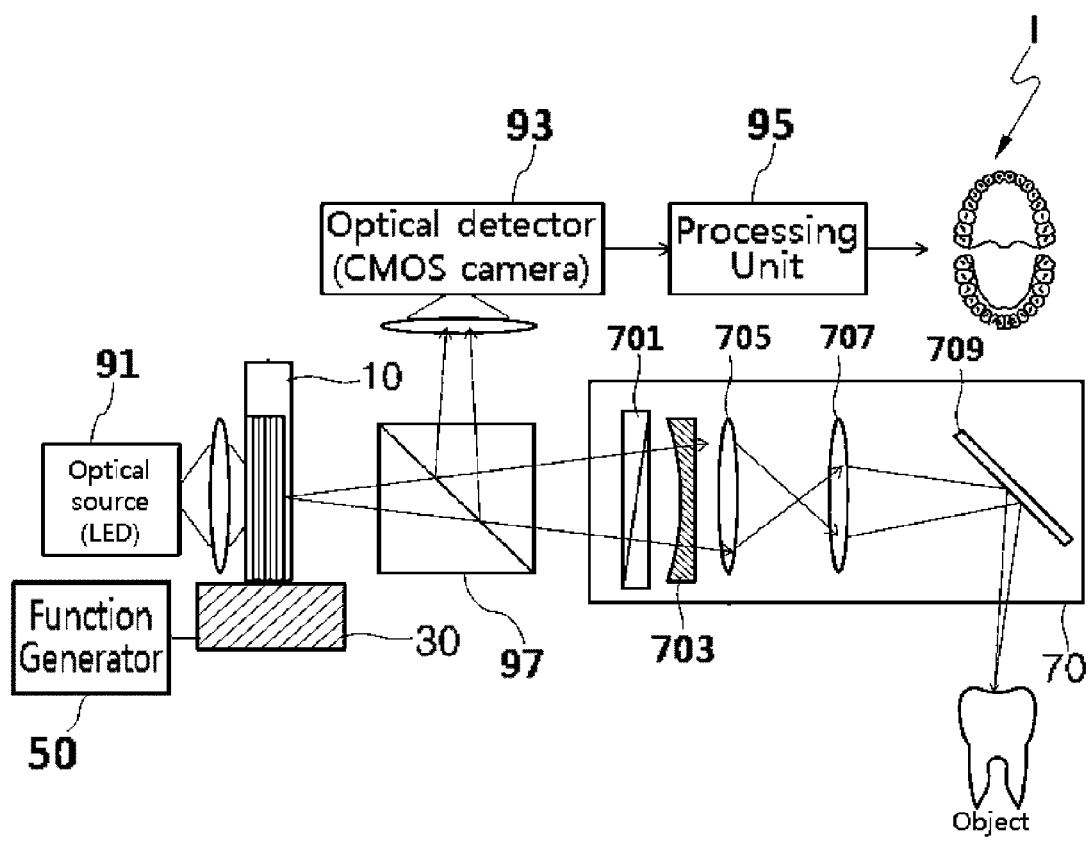
FIG. 2 is a view showing an oral cavity scan device according to an embodiment of the present invention.

FIG. 2 is a view showing an oral cavity scan device 1 according to an embodiment of the present invention. Referring to FIG. 2, the oral cavity scan device 1 may include an optical source 91, a pattern mask 10, a piezoelectric plate 30, a power supply unit 50, a lens unit 70, an optical detector 93, a processing unit 95, and a beam splitter 97.

The optical source 91 may use red, green, blue LED and LD.

The pattern mask 10 may convert parallel light incident thereto into structured light. The pattern mask 10 may include a light transmission line 101 through which parallel light passes and a light shielding line 103 blocking the parallel light.

The light transmission line 101 and the light shielding line 103 are alternately arranged in the pattern mask 10. The light transmission line 101 and the light shielding line 103 may be provided in a vertical direction. The pattern mask is provided at a predetermined position in a vertical direction. The pattern mask 10 may generate pattern shape light when laser light passes through the pattern mask.

Structured light is light having a specific pattern and being incident to a target subject. The structured light is light passing the pattern mask 10 to apply a two-dimensional scanning to the subject. There are various methods of forming a pattern of structured light; however, the present invention uses a method of forming structured light by moving the pattern mask 10. The structured light may have even brightness of a grid pattern.

The piezoelectric plate 30 may have mechanical vibrations on a surface thereof due to an AC voltage applied to the piezoelectric plate. In addition, the piezoelectric plate 30 may move the pattern mask 10 in a longitudinal direction of the piezoelectric plate 30 by using the mechanical vibrations generated on the surface of the piezoelectric plate. The longitudinal direction means a direction in which the piezoelectric plate 30 extends. The pattern mask 10 is moved by the piezoelectric plate 30 in the longitudinal direction, which is the direction of that the piezoelectric plate 30 extends, within a predetermined range.

Figure 3:
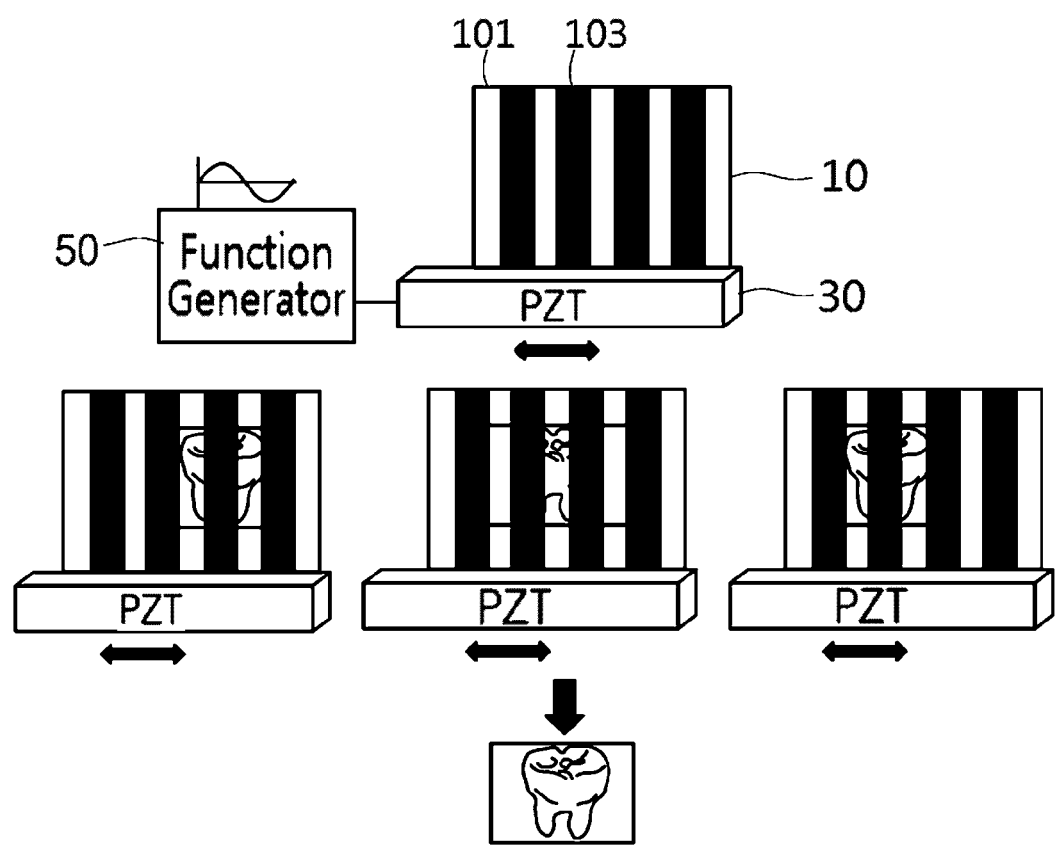
FIG. 3 is a view showing a pattern mask and a piezoelectric plate according to an embodiment of the present invention.

FIG. 3 is a view showing the pattern mask 10 and the piezoelectric plate 30 according to an embodiment of the present invention. Referring to FIG. 3, the piezoelectric plate 30 may be coupled to the pattern mask 10 in order to move the pattern mask 10. According to the embodiment of the present invention, the piezoelectric plate 30 may be perpendicularly coupled to a lower end of the pattern mask 10. When an AC voltage is applied to the piezoelectric plate 30, the piezoelectric plate 30 generates the mechanical vibrations, and the pattern mask 10 perpendicularly coupled to the piezoelectric plate may be operated in response to the mechanical vibrations of the piezoelectric plate 30.

The piezoelectric plate 30 uses a piezoelectric effect of piezoelectric ceramics, and thus, it is impossible to use the piezoelectric plate itself. When applying an electric field in a desired direction, the piezoelectric plate generates vibrations. The piezoelectric plate may be operated by receiving voltage of the power supply unit 50. An alternating current may include a typical household AC voltage or a pulse-shape AC voltage having a periodic function. In addition, the piezoelectric plate 30 may be controlled depending on levels and an applied direction of an AC voltage, and the piezoelectric plate may be used in the present invention that requires high torque and low speed.

The piezoelectric plate 30 may be a PZT ceramic element generating mechanical vibrations on a surface thereof by using an AC voltage applied thereto. Plumbum zirconate titanate (PZT) has proper piezoelectric characteristics, and is used as energy conversion material in a piezoelectric structure.

The piezoelectric plate 30 may be provided in a plate shape having an extended length, and moves the pattern mask 10 according to the embodiment of the present invention. When an electric field is applied to the piezoelectric plate 30 including a ceramic element which is an elastic body, mechanical extension and contraction are generated in a direction perpendicular to the electric field depending on polarization directions. When an AC voltage is applied to the piezoelectric plate 30, mechanical vibrations are generated in the shape of a sine wave. Consequently, the pattern mask 10 may have same periods and may be moved within a predetermined range by generating vibrations. According to the embodiment of the present invention, the pattern mask may be moved in periods of 100 µm.

Therefore, when the pattern mask 10 is periodically moved in the case that the optical source 91 has the same levels, the optical detector 93 may obtain an image of a specific position.

Figure 4:
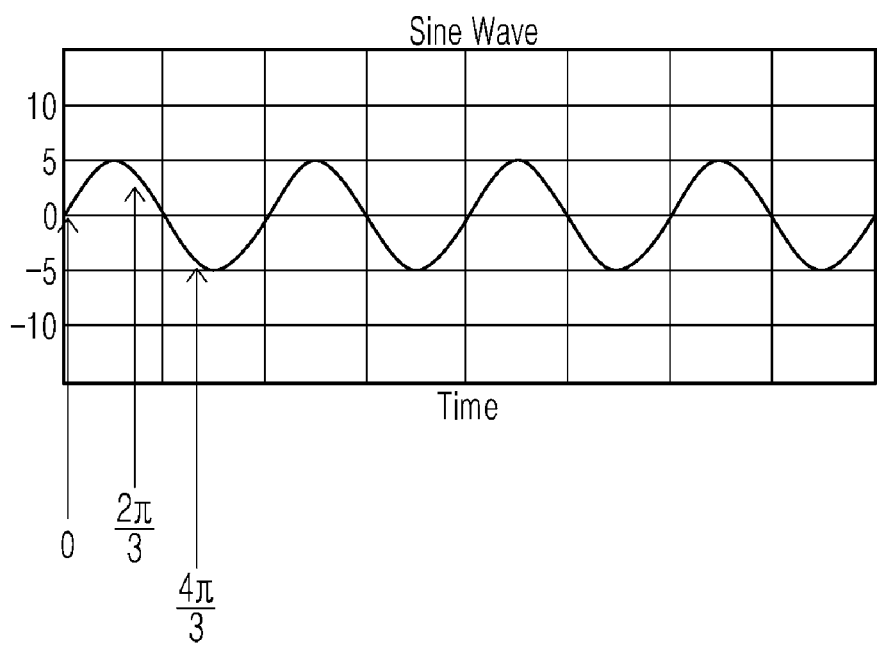
FIG. 4 is a view showing a case of obtaining an image of the pattern mask according to an embodiment of the present invention.

FIG. 4 is a view showing a process of obtaining an image of the pattern mask 10 according to an embodiment of the present invention. Referring to FIG. 4, the image is obtained by dividing the pattern into three patterns. According to the embodiment of the present invention, it is possible to form 3 to 10 patterns in order to obtain the image. The narrower intervals between the patterns are, the better the resolution is, but the lower intensity response characteristics are. Therefore, the intervals between the patterns may be properly adjusted depending on a purpose of measuring an image.

The power supply unit 50 may apply an AC voltage to the piezoelectric plate 30. It is possible to apply a traveling wave in the longitudinal direction of the piezoelectric plate 30, and to generate the mechanical vibrations of the piezoelectric plate 30 depending on an applied waveform as described above.

The beam splitter 97 may divide the structured light depending on wavelength and levels of light. The structured light is incident to the beam splitter 97, and passes through the beam splitter, and is incident to the lens unit 70. The beam splitter 97 reflects a portion of the structured light, and may include a reflector or any other optical devices through which the remaining portion passes. It is possible to obtain two output beams by using birefringence of crystals, and the two output beams have respective vibration directions perpendicular to each other.

The lens unit 70 may include a polarizing lens 701 preventing diffused refection, an offset lens 703 having a concave curvature to which the structured light is incident, a variable focus lens 705 adjusting a focal distance by using voltage or current, a focusing lens 707 focusing a focal point of the structured light, and a reflection mirror 709 reflecting the structured light in the direction toward the subject.

The lens unit 70 is positioned between the structured light and the subject, and provides the structured light with a route to the subject. The lens unit may be adjusted to obtain an image of teeth by adjusting the focal distance of the structured light.

When directly using the structured light, the polarizing lens 701 may block diffused reflections, reflected light, etc. that are caused by metallic teeth. The polarizing lens 701 may receive only a certain amount that is ¼ wavelength of light passing through the polarizing lens 701 by arranging fine lines in accurate intervals (three hundred thousand/$cm^2$). The polarizing lens 701 may prevent diffused reflections and reflected light from metal by passing only light that enters straight between minutely arranged lines.

The offset lens 703 may be formed with a concave curvature, and the structured light may be incident to the offset lens. The offset lens 703 may be positioned in front of the variable focus lens 705 so as to provide the oral cavity scan device 1 in a small size. The offset lens 703 may reduce the focal distance of reflected structured light.

The structured light having reduced focal distance may be incident to the variable focus lens 705, and the variable focus lens 705 may be controlled by voltage or current. The variable focus lens 705 may include liquid, and the liquid may include an electrolyte.

The variable focus lens 705 may include insulative liquid and conductive liquid. Dispersion of both the insulative liquid and the conductive liquid varies depending on levels of applied driving voltage or current, thereby adjusting the focal distance. Depending on the levels of applied driving voltage or current, the variable focus lens 705 may change a curvature of an interface including an electrolyte, thereby adjusting the focal distance of the lens.

The variable focus lens 705 may include a first liquid layer that is conductive, a second liquid layer that is insulative, and a plurality of electrodes to which voltage or current is applied. When voltage or current is applied to the plurality of electrodes, the variable focus lens 705 may control the reduced focal distance by adjusting the first and second liquid layers that are arranged to be parallel to each other. According to the embodiment of the present invention, the first liquid layer, the second liquid layer, and the plurality of electrodes are included, without being limited thereto. In addition, a plurality of conductive liquid layers, insulative liquid layers, and resistive layers may be included.

The first liquid layer and the second liquid layer may be arranged to be parallel to the surface of the variable focus lens 705. The plurality of electrodes may be arranged around the variable focus lens 705. When voltage or current is applied, it is possible to adjust arrangements of internal components of the first and second liquid layers.

By inserting the variable focus lens 705, the oral cavity scan device 1 may be provided in a compact size, and may reduce mechanical movements. A mechanical actuator, which has high manufacturing costs, is unnecessary, and movements (mechanical movements) decrease, thereby reducing dust entering into the oral cavity scan device 1. In addition, the variable focus lens is lighter than a glass lens, and has effective power consumption and milliseconds of fast response speed.

The variable focus lens 705 may adjust the focal distance by using proper voltage or current in order to accurately scan teeth. The variable focus lens 705 may be adjusted so as to start scanning from an upper surface or a lower surface of teeth.

The reflection mirror 709 may reflect the structured light which passed the pattern mask 10, and may direct the reflected structured light to the subject. A reflection angle of the reflection mirror 709 may be 45° angles.

The optical detector 93 may photograph an image of reflected light from the subject, namely, an image of reflected light which passed the beam splitter 97. The optical detector 93 may convert the photographed image into an electrical signal, and may transmit the electrical signal to the processing unit 95. The optical detector 93 may use a CMOS image sensor performing noncontact three-dimensional measurement represented by a phase shift method or a space encoding method.

The processing unit 95 may receive an image photographed at the optical detector 93. The processing unit 95 may include a wireless transmission device, and may receive an image through a wireless network. The processing unit 95 may receive at least one image photographed at the optical detector 93, and may obtain the received image to obtain a three-dimensional image.

While the representative embodiments of the present invention have been described above, the embodiments are only examples of the invention, and it will be understood by those skilled in the art that the invention can be modified in various forms without departing from the technical spirit of the invention. Therefore, the scope of the present invention should not be defined as being limited to the embodiments, but should be defined by all changes and modifications that are derived from the appended claims and equivalents thereof.

DESCRIPTION OF MAIN REFERENCE NUMERALS OF DRAWINGS

1: oral cavity scan device
10: pattern mask    30: piezoelectric plate

-continued

| | |
|---|---|
| 50: power supply unit | 70: lens unit |
| 91: optical source | 93: optical detector |
| 95: processing unit | 97: beam splitter |
| 101: light transmission line | 103: light shielding line |
| 701: polarizing lens | 703: offset lens |
| 705: variable focus lens | 707: focusing lens |
| 709: reflection mirror | |

The invention claimed is:

1. An oral cavity scan device obtaining a three-dimensional shape of teeth by using structured light, the device comprising:
a pattern mask converting parallel light incident thereto into the structured light;
a piezoelectric plate where a mechanical vibration is generated on a surface thereof by an AC voltage applied thereto; and
a power supply unit applying the AC voltage to the piezoelectric plate,
wherein the piezoelectric plate moves the pattern mask in a longitudinal direction of the piezoelectric plate by using the mechanical vibration generated on the surface of the piezoelectric plate.

2. The device of claim 1, wherein the piezoelectric plate is a PZT (plumbum zirconate titanate) ceramic element.

3. The device of claim 1, wherein the pattern mask comprises:
a light transmission line through which the parallel light passes; and
a light shielding line blocking the parallel light,
wherein the light transmission line and the light shielding line are alternately arranged in the pattern mask.

4. The device of claim 3, wherein the piezoelectric plate is a PZT (plumbum zirconate titanate) ceramic element.

5. The device of claim 1, further comprising:
an offset lens to which the structured light is incident, with a concave curvature formed in the offset lens; and
a reflection mirror reflecting the structured light in a direction toward a subject,
wherein the offset lens reduces a focal distance of the structured light.

6. The device of claim 5, wherein the piezoelectric plate is a PZT (plumbum zirconate titanate) ceramic element.

7. The device of claim 5, further comprising:
a variable focus lens adjusting the reduced focal distance of the structured light penetrating the offset lens.

8. The device of claim 7, wherein the variable focus lens enables reflected light reflected from the subject to be incident to the offset lens so as to obtain an image of the teeth.

9. The device of claim 7, wherein the piezoelectric plate is a PZT (plumbum zirconate titanate) ceramic element.

10. The device of claim 8, wherein the piezoelectric plate is a PZT (plumbum zirconate titanate) ceramic element.

\* \* \* \* \*